United States Patent

Vega et al.

[11] Patent Number: 6,133,187
[45] Date of Patent: *Oct. 17, 2000

[54] HETERGENEOUS METALLOCENE CATALYSTS AND USE THEREOF IN OLEFIN POLYMERIZATION PROCESS

[75] Inventors: Wilfried Michiels Vega, Alcala de Henares; Pilar Lafuente Cañas, Madrid; Antonio Muñoz-Escalona Lafuente, Pozuelo de Alarcon; Gerardo Hidalgo Llinas; Jose Sancho Royo, both of Madrid; Luis Mendez Llatas, Mostoles, all of Spain

[73] Assignee: Repsol Quimica S.A., Madrid, Spain

[ * ] Notice: This patent is subject to a terminal disclaimer.

[21] Appl. No.: 09/174,997

[22] Filed: Oct. 19, 1998

Related U.S. Application Data

[62] Division of application No. 08/958,880, Oct. 27, 1997, Pat. No. 5,824,620, which is a continuation of application No. 08/691,308, Aug. 2, 1996, abandoned.

[30] Foreign Application Priority Data

Aug. 3, 1995 [ES] Spain .................................. 9501586

[51] Int. Cl.[7] .............................. B01J 31/00; B01J 37/00; C08F 4/02; C08F 4/60
[52] U.S. Cl. .......................... 502/103; 502/117; 502/118; 502/121; 502/122; 502/124; 502/125; 502/128; 502/152; 502/158
[58] Field of Search .................................. 502/103, 117, 502/118, 121, 122, 124, 125, 128, 152, 158

[56] References Cited

U.S. PATENT DOCUMENTS

| | | |
|---|---|---|
| 5,057,475 | 10/1991 | Canich et al. . |
| 5,202,398 | 4/1993 | Antberg et al. .......................... 502/120 |
| 5,391,789 | 2/1995 | Rohrmann . |
| 5,416,228 | 5/1995 | Ewen et al. . |
| 5,504,232 | 4/1996 | Winter et al. . |
| 5,627,246 | 5/1997 | Langhauser et al. . |
| 5,824,620 | 10/1998 | Vega et al. .............................. 502/117 |
| 5,892,079 | 4/1999 | Wilson, Jr. .............................. 502/103 |

FOREIGN PATENT DOCUMENTS

| | | |
|---|---|---|
| 0 206 794 | 12/1986 | European Pat. Off. . |
| 0 260 130 | 3/1988 | European Pat. Off. . |
| 0 277 004 | 8/1988 | European Pat. Off. . |
| 0 293 815 | 12/1988 | European Pat. Off. . |
| 0 314 797 | 5/1989 | European Pat. Off. . |
| 0 323 716 | 7/1989 | European Pat. Off. . |
| 0 361 866 | 4/1990 | European Pat. Off. . |
| 0 367 503 | 5/1990 | European Pat. Off. . |
| 0 368 644 | 5/1990 | European Pat. Off. . |
| 0 426 637 | 5/1991 | European Pat. Off. . |
| 0 474 391 | 3/1992 | European Pat. Off. . |
| 0 628 566 | 12/1994 | European Pat. Off. . |
| 3718888 | 12/1988 | Germany . |
| 2608863 | 6/1989 | Germany . |
| 3840772 | 6/1990 | Germany . |

OTHER PUBLICATIONS

Ciruelos, et al. (including Royo), Organometallics 1995, 14, 177–185.

Sinn, H. and Kaminsky, W. (Adv. Organomet. Chem. 18, 99–155, 1980).

Chien, J.C.W., Makromol. Chem., Macromol. Symp., 66, 141–156, 1993.

*Primary Examiner*—Mark L. Bell
*Assistant Examiner*—J. Pasterezyk
*Attorney, Agent, or Firm*—Ladas & Parry

[57] ABSTRACT

A catalyst comprising a cocatalyst and a catalyst component obtained by contacting a silicon-containing metallocene compound with an inorganic support to chemically bond the metallocene compound to the inorganic support, wherein the silicon-containing metallocene compound has a formula (I):

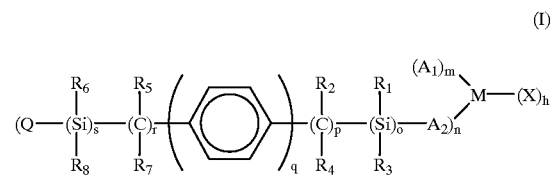

(I)

wherein:

M is a metal selected from [the group consisting of] group 4, 5, or 6 of the periodic table;

each X is independently selected from the group consisting of hydrogen, halogen, $C_1$–$C_{10}$ alkyl, $C_1$–$C_{10}$ alkoxy, $C_6$–$C_{10}$ aryl, $C_6$–$C_{10}$ aryloxy, $C_2$–$C_{10}$ alkenyl, $C_7$–$C_{40}$ arylalkyl, $C_7$–$C_{40}$ alkylaryl, and $C_8$–$C_{40}$ arylalkenyl;

$A_1$ and $A_2$ are independently selected from the group consisting of cyclopentadienyl, substituted cyclopentadienyl, indenyl, fluorenyl, substituted indenyl, and substituted fluorenyl, wherein the substituents are independently $C_1$–$C_{10}$ linear or branched alkyl, $C_5$–$C_7$ cycloalkyl, optionally substituted by an alkyl group, $C_6$–$C_{10}$ aryl, $C_6$–$C_{10}$ aryloxy, $C_2$–$C_{10}$ alkenyl, $C_7$–$C_{40}$ arylalkyl, $C_7$–$C_{40}$ alkylaryl, or $C_8$–$C_{40}$ arylalkenyl.

23 Claims, No Drawings

HETERGENEOUS METALLOCENE CATALYSTS AND USE THEREOF IN OLEFIN POLYMERIZATION PROCESS

This is a divisional of application Ser. No. 08/958,880 filed on Oct. 27, 1997, now U.S. Pat. No. 5,824,620, which is a continuation of application Ser. No. 08/691,308, filed on Aug. 2, 1996, now abandoned.

The present invention relates to heterogeneous metallocene catalysts and use thereof in an olefin polimerization process.

TECHNICAL BACKGROUND

Metallocene compounds such as bis(cyclopentadienyl) titanium dialkyl or bis(cyclopentadienyl)zirconium dialkyl in combination with aluminium alkyls are well known homogeneous olefin polymerization catalysts. DE-2,608,863 describes the use of bis(cyclopentadienyl) titanium dialkyl in combination with trialkylaluminium and a controlled amount of water.

The controlled hydrolysis of aluminium alkyls gives rise to the formation of species containing an Al—O bond (aluminoxane) which are effective co-catalysts of metallocenes. Kaminski (Adv. Organomet. Chem. 18, 99, 1980) disclosed that aluminoxanes in combination with dichlorometallocenes produce catalytic systems very active in ethylene polymerization.

However, it is also possible (Turner, EP 277004 and Ewen et al. EP 426637) the use of co-catalysts based on bulky boron compounds which, acting as non-coordinative anions, stabilize the cationic metallocene without preventing the incorporation of the olefin in the polymerization process.

The most olefin polymerization processes make use of homogeneous catalytic systems. This results in very high activities. However industrial processes require heterogenous systems which on one hand produce polymers having controlled morphology, on the other hand maintain the activity of homogeneous systems.

EP 206794 discloses heterogeneous catalysts obtained by simultaneous or subsequent (in any order) addition of aluminoxane and metallocene onto an inorganic support.

This process, according to EP 260130, is also applicable to multicomponent systems, that is catalysts containing either several metallocenes or a metallocene and a non-metallocene transitional metal compound. In this way polyolefins having multimodal molecular weight distribution are obtained.

EP 361866, EP 323716, EP 367503, EP 368644 and U.S. Pat. No. 5,057,475 describe the preparation of a heterogeneous catalytic system composed by an aluminoxane and a metallocene characterized in that the aluminoxane is generated in situ by reaction of a trialkylaluminium with undehydrated silica. The use thereof in Ó-olefin polymerization results in high activities.

Another well known technique used in the preparation of heterogeneous catalysts is chemical modification of the inorganic support. EP 474391 and EP 314797 disclose a process wherein the support, before addition of the metallocene, is treated with an organoaluminium compound which reacts with the hydroxy groups present on the silica surface.

The above described methods produce heterogeneous catalysts which present the drawback that the catalyst is not tightly bonded to the support so that separation of the metallocene from the inorganic support occurs.

Consequently it has been looked for the formation of a chemical bond between the support and the metallocene. A possible solution is the formation of a chemical bond by reacting a functionalized metallocene and a partly dehydrated silica. EP 293815 and DE 3718888 disclose a process for the preparation of a supported catalyst wherein the chemical bond between support and metallocene is obtained by reaction of an alkoxy group bond to silicon and the hydroxy group of the support. The synthesis of this catalyst is difficult and very low yields were obtained. Furthermore the catalytic activity in Ó-olefin polymerization is quite low.

DE 3840772 discloses the use of metallocenes functionalized by vinyl groups bonded to the cyclopentadienyl ring. The double bond is further reacted with polysiloxanes. This method presents the drawback of the use of an additional catalyst, essential for reacting the double bond with siloxane. This requires a further purification step in order to remove the catalyst.

According to EP 628566 it is possible to prepare heterogeneous catalysts by reacting ligands directly bonded to the cyclopentadienyl ring with alkyllithium and metal halides of formula $MX_4$ (wherein M is a transition metal and X is halide). This process results in catalysts wherein the metallocene is very tightly bonded to the support. They are used in olefin polymerization in combination with alumoxane. Also in this case the catalyst component needs to be purified in order to remove the residue of the compounds used in the preparation of the catalyst component.

In the present invention a method for obtaining heterogeneous catalyst components is described wherein a properly functionalized metallocene is contacted with an inorganic support.

The present invention also discloses new metallocenes particularly suitable for the preparation of the supported catalyst component of the present invention.

A further object of the present invention is the use of these catalyst components in combination with a cocatalyst for polymerizing Ó-olefins.

A further object of the present invention is the use of specific compounds for the modification of the inorganic support.

The catalyst components according to the invention present a very strong bond between the metallocene and the support without losing catalytic activity. Furthermore the by-products resulting from the synthesis of the catalyst component do not reduce the catalytic activity and thus do not need to be removed. The so obtained catalyst polymerizes Ó-olefins in high yields and without phenomena of leaching of the metallocene from the support.

DETAILED DESCRIPTION OF THE INVENTION

The present invention relates to a catalyst component obtainable by contacting a metallocene compound with an inorganic support, wherein the metallocene compound A has formula (I):

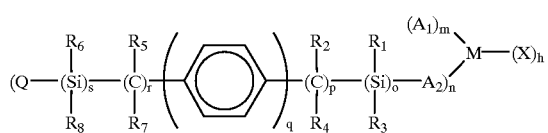

(I)

wherein:
- M is a metal of group 4, 5 or 6 of the periodic table, preferably Ti, Zr or Hf.
- Each X is independently selected from hydrogen, halogen, $C_1$–$C_{10}$ alkyl, $C_1$–$C_{10}$ alkoxy, $C_6$–$C_{10}$ aryl, $C_6$–$C_{10}$ ariloxy, $C_2$–$C_{10}$ alkenyl, $C_7$–$C_{40}$ arylalkyl, $C_7$–$C_{40}$ alkylaryl, $C_8$–$C_{40}$ arylalkenyl.
- $A_1$ and $A_2$ are independently selected from cyclopentadienyl, substituted cyclopentadienyl, indenyl, fluorenyl, substituted indenyl and substituted fluorenyl, wherein the substituents are independently selected from $C_1$–$C_{10}$ linear or branched alkyl, $C_5$–$C_7$ cycloalkyl, optionally substituted by an alkyl group, $C_6$–$C_{10}$ aryl, $C_6$–$C_{10}$ ariloxy, $C_2$–$C_{10}$ alkenyl, $C_7$–$C_{40}$ arylalkyl, $C_7$–$C_{40}$ alkylaryl, $C_8$–$C_{40}$ arylalkenyl.
- $R_1, R_2, R_3, R_4, R_5, R_6, R_7, R_8$ are independently selected from hydrogen, $C_1$–$C_{10}$ linear or branched alkyl, $C_5$–$C_7$ cycloalkyl optionally substituted by a $C_1$–$C_6$ alkyl, $C_6$–$C_{10}$ aryl, $C_2$–$C_{10}$ alkenyl, $C_7$–$C_{40}$ arylalkyl, $C_7$–$C_{40}$ alkylaryl, $C_8$–$C_{40}$ arylalkenyl. Furthermore $R_6$ and $R_8$ can be Q wherein Q is selected from halogen, amino, alkylamino, hydroxy. Preferably Q is F, Cl, Br or I.
- o, p, q, r, s can vary from 0 to 10.
- m=0 or 1 n=1 or 2 h=2 or 3 and such that m+n+h=4.

Metallocenes according to formula (I) are prepared according to Royo et al., Organometallics, 14, 177,(1995), except when the metallocenes are monofunctionalized. In this case the use of trichloromonocyclopentadienyl transition metal compounds is required.

Metallocenes compounds useful for the preparation of catalyst components according to the invention are for example:

(Chlorodimethylsilylcyclopentadienyl)cyclopentadienyl zirconium dichloride.
Bis(Chlorodimethylsilylcyclopentadienyl) zirconium dichloride.
Bis(Chlorodimethylsilylcyclopentadienyl) zirconium dimethyl.
(Bromodimethylsilylcyclopentadienyl)cyclopentadienyl zirconium dichloride.
Bis(Bromodimethylsilylcyclopentadienyl) zirconium dichloride.
Chlorodimethylsilylcyclopentadienyl zirconium trichloride.
(2(Chlorodimethylsilyl)ethylcyclopentadienyl) cyclopentadienyl zirconium dichloride.
(3(Chlorodimethylsilyl)propylcyclopentadienyl) cyclopentadienyl zirconium dichloride.
(Chlorodimethylsilylcyclopentadienyl)cyclopentadienyl zirconium dimethyl.
(Bromodimethylsilylcyclopentadienyl)cyclopentadienyl zirconium dimethyl.
Bis(Bromodimethylsilylcyclopentadienyl) zirconium dimethyl.
(2(Chlorodimethylsilyl)ethylcyclopentadienyl) cyclopentadienyl zirconium dimethyl.
(3(Chlorodimethylsilyl)propylcyclopentadienyl) cyclopentadienyl zirconium dimethyl.
(Chlorodimethylsilylcyclopentadienyl)cyclopentadienyl titanium dichloride.
Bis(Chlorodimethylsilylcyclopentadienyl) titanium dichloride.
(Chlorodimethylsilylcyclopentadienyl) fluorenyl zirconium dichloride.

The inorganic support according to the present invention contains hydroxy-groups.

Illustrative, but not limiting, examples of supports useful in the present invention are the following: silicates, carbonates, phosphates, clays, metaloxides and mixtures thereof. Most preferred are silica, alumina, silica-alumina, silica titanates, silica vanadates, silica chromates, aluminium phosphates, phosphated silica and mixtures thereof.

The surface area of the inorganic support is 10–1000 $m^2/g$, preferably 150–650 $m^2/g$, the pore volume is 0.2–4.0 $cm^3/g$, preferably 0.6–2.7 $cm^3/g$, the average particle size is 1–1000 micron, preferably 5–100 micron.

The water contained in the support is optionally removed before reacting the support with functionalized metallocene. The dehydration step is performed by heating the support in a furnace in an inert atmosphere at from 120° C. to 1000° C. (preferably from 200 to 800° C.). The amount of hydroxy groups on the support can be measured by titration with n-butylmagnesium chloride or triethylaluminium.

The concentration of hydroxy-groups depends on the dehydration temperature and may vary from 0,1 to 5 mmol OH/g support, preferably 0.3 to 3 mmol OH/g support or from 0,1 to 7 OH groups/$nm^2$, preferably 0.5 to 5 OH groups/$nm^2$. Once dehydrated the support has to be stored under inert atmosphere (nitrogen or argon) to protect it from oxygen and humidity.

The inorganic support is used as such or is previously modified by reaction of the hydroxy-groups with compounds of formula (II):

$$(R_9)_v\text{—}\underset{(R_{14})_w}{\overset{(R_{13})_z}{\underset{|}{\overset{|}{Si}}}}\text{—}(O\text{—}\underset{R_{11}}{\overset{R_{10}}{\underset{|}{\overset{|}{Si}}}})_t\text{—}(R_{12})_u\text{—}Z \quad (II)$$

wherein:
- $R_9$ is halogen or OR, R being $C_1$–$C_{10}$ linear or branched alkyl, $C_5$–$C_7$ cycloalkyl optionally substituted by a $C_1$–$C_6$ alkyl, $C_6$–$C_{10}$ aryl, $C_2$–$C_{10}$ alkenyl, $C_7$–$C_{40}$ arylalkyl, $C_7$–$C_{40}$ alkylaryl, $C_8$–$C_{40}$ arylalkenyl.
- $R_{10}, R_{11}, R_{12}, R_{13}, R_{14}$, are independently selected from hydrogen, $C_1$–$C_6$ lineal or branched alkyl, $C_5$–$C_7$ cycloalkyl, $C_6$–$C_{10}$ aryl, $C_2$–$C_{10}$ alkenyl, $C_7$–$C_{40}$ arylalkyl, $C_7$–$C_{40}$ alkylaryl, $C_8$–$C_{40}$ arylalkenyl, $C_1$–$C_{10}$ alkoxy, aryloxy.
- Z is $NH_2$, NHR, SH, OH, PHR, Cl, Br or I.
- v+z+w=3 with v different from 0
- t and u are from 0 to 10.

Examples of compounds of formula (II) are the following: 3-mercaptopropyltrimethoxysilane, 3-aminopropyltrimethoxysilane, N-phenylaminopropyltrimethoxysilane, N-methylaminopropyltrimethoxysilane, 3-chloropropyltrimethoxysilane, and N-aminopropyldimethoxymethylsilane.

The chemical modification of the inorganic support is preferably carried out in a hydrocarbon (toluene or heptane).

The reaction temperature may vary in a large range and is preferably between room temperature and the boiling temperature of the solvent. The reaction time is not essential but is preferably from 2 to 24 hours, most preferably from 4 to 12 hours.

The reaction between functionalized metallocene and inorganic support (chemically modified or not) is preferably carried out in a hydrocarbon (e.g. toluene or heptane). The temperature may vary in a wide range but is preferably from room temperature up to boiling temperature of the hydrocarbon. The reaction time is also not essential but is preferably from 30 minutes to 24 hours.

Once the reaction is completed (no more gas evolution) the catalyst component is filtered and washed with toluene several times to remove the unreacted metallocene.

The catalyst component is dried under vacuum and stored in an inert atmosphere, remaining active for a long period of time. When the metallocene used in the preparation of the catalyst component is bifunctionalized, the obtained catalyst components are the following:

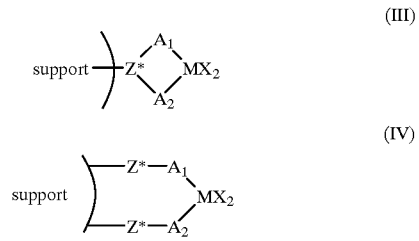

(III)

(IV)

When the metallocene used in the preparation of the catalyst component is monofunctionalized, the obtained catalyst components are the following:

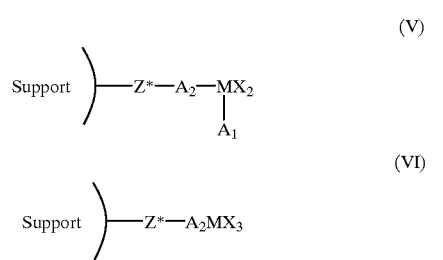

(V)

(VI)

wherein $Z^*$ corresponds to Z of formula (II) modified by chemical reaction between the functionalized metallocene catalyst and the functional groups of the support.

The chemical bond between support and metallocene provides a catalyst which maintains the structure of the active species and, in the presence of a cocatalyst, is very active in olefin polymerization.

The cocatalyst used for activating the catalyst component is selected from methylaluminoxane (MAO), modified methylaluminoxane (MMAO), and boron compounds such as N,N-dimethylanilinium tetrakis(pentafluorophenyl)borate or trispentafluorophenylborane. If the cocatalyst used is a boron compound, the metallocene needs to be converted into an alkyl derivative. The alkylation reaction can be carried out by using alkylating agents decribed in literature, such as aluminium alkyls (TIBA), MAO, alkyl compounds of alkali metals, such as methyl lithium, butyl lithium and the like, or can be alkylated "in situ" by adding small amounts of aluminium alkyls (TIBA, TEA) and subsequent formation of the cation by addition of the boron compound (Chien, J. C. W., Makromol. Chem., Macromol. Symp., 66,141–156, (1993)).

The catalytic systems of the present invention are useful for the homo- and copolymerization of $C_2$–$C_{20}$ Ó-olefins in the gas phase, in slurry or in solution, at a pressure of from 1 to 2000 atm, at a temperature of from –40° C. to 280° C. The polymerization time depends on the process used and might generally vary between 20 seconds and 6 hours.

The concentration of the transition metal in the reaction medium can vary in a wide range but is preferably between $1.7 \times 10^{-6}$ M and $5 \times 10^{-3}$ M, most preferably between $8.3 \times 10^{-6}$ M and $5 \times 10^{-4}$ M.

When aluminoxane is used as a cocatalyst, the molar ratio Al/Me of the metallocene is preferably comprised between 10 and 10,000, most preferably between 100 and 2000.

When a boron compound is used as a cocatalyst, the molar ratio B/Me is preferably comprised between 0.5 and 10, most preferably between 0.9 and 5.

The molecular weight of the polymer can be adjusted by varying the polymerization temperature, the concentration of the catalyst in the reaction medium, the molar ratio cocatalyst/catalyst or by feeding hydrogen to the reactor.

The process is applicable to any olefin polymerizable by using a Ziegler-Natta catalyst, it is however particularly suitable for homopolymerizing Ó-olefins having 2 to 20 carbon atoms such as ethylene, propylene, 1-butene, 1-hexene, 4-methyl-1-pentene and the like, as well as cyclic monomers.

The process is also suitable for copolymerizing ethylene with Ó-olefins having 3 to 20 carbon atoms, preferably from 3 to 8, such as propylene, 1-butene, 1-hexene, 4-methyl-1-pentene, 1-octene and the like, as well as cyclic monomers, or mixtures of two or more of these comonomers.

The molar ratio between the comonomer and ethylene can vary in a wide range; it is however preferred to use a range from 1:1 to 5:1. In this way polymers having density from 0.860 to 0.960 g/cm³ are obtained.

EXAMPLES

The following examples are presented solely for purposes of illustration and should not be construed as limiting the invention.

Examples 1 and 2(a, b and c) relates to the preparation of the support of the catalyst component and its use for obtaining heterogeneous catalysts according to the present invention.

Example 1

This example illustrates the preparation of an inorganic support wherein the amount of hydroxy-group has been controlled by calcination. The calcined support is used for preparing a supported metallocene catalyst. In an inert gas fluidized bed calcination furnace, a sample of support is introduced. The furnace is heated at a speed of 10° C./min up to nominal calcination temperature. The sample is kept for 4 hours at this temperature and is afterwards cooled down, always under inner atmosphere. Eventually, the sample is discharged in a container previously flushed with inert gas and dried. The amount of residual hydroxy group can be determined by the amount of ethane formed in the stoichiometric reaction of the hydroxy group with triethyl aluminium. Table I shows the relationship between calcination temperature and amount of hydroxy group.

TABLE I

| Support | Calcination T | mmol OH/g support |
|---|---|---|
| $SiO_2$ | 200° C. | 2.03 |
| " | 400° C. | 1.56 |
| " | 800° C. | 0.78 |
| $AlPO_4$ | 200° C. | 1.21 |
| " | 400° C. | 0.95 |
| " | 800° C. | 0.65 |

Example 2A

This example illustrates the preparation of an inorganic support by chemical modification of the silica by incorporation of $NH_2$ groups by reaction with a compound with a $NH_2$ group.

In a 250 ml glass reactor equipped with a mechanical stirrer and immersed in a thermostatic bath 16 g of silica previously calcined at 300° C. (according to Example 1) are added. The concentration of OH groups is 1.60 mmol/g. The silica is slurried with 50 ml of toluene and is further added with 0.024 moles of 3-aminopropyltrimethoxysilane ((MeO)$_3$Si(CH$_2$)$_3$NH$_2$)). The reaction mixture is kept under reflux for 12 hours. The solid product is filtered, washed several times with the dry toluene (5×100 ml). The silica is dried under vacuum during 12 hours. The nitrogen content is 1.73%.

Example 2B

This example illustrates the preparation of an inorganic support by chemical modification of the silica by incorporation of NHPh groups by reaction with a compound with a NHPh group. The preparation of example 2A was followed but using 18 g of silica calcined at 300° C. (according to example 1), with a concentration of OH groups of 1.90 mmols per gram of inorganic support and 0.034 moles of N-phenylaminopropyl trimethoxysilane ((MeO)$_3$Si(CH$_2$)$_3$NPh). The reaction mixture is kept under reflux for 12 hours. The solid product is filtered, washed several times with dry toluene. The nitrogen content is 0.58 mmoles N/g.

Example 2C

This example illustrates the preparation of an inorganic support to obtain a metallocene catalyst supported by chemical modification of the support with SH groups. The preparation of example 2A is followed but 21 g of silica previously calcined at 300° C. (following example 1) is used, with a OH groups concentration of 1.90 mmoles per g of inorganic support and furtherly adding 0.040 moles of 3-mercaptopropyl trimethoxysilane ((MeO)$_3$Si(CH$_2$)$_3$SH). The reaction mixture is kept under reflux for 12 hours. The solid product is filtered, washed several times with dry toluene. The sulphur content is 1.86% by weight.

Examples 3–8 relate to the preparation of catalyst components according to the present invention. Metallocenes used in the preparation were synthetized according to the method disclosed in Organometallics, 14, 177, (1995).

Example 3

This example illustrates the preparation of a catalyst component supported onto an inorganic support containing a controlled amount of OH groups. The impregnation reaction of the metallocene onto the inorganic support is carried out in a 250 ml glass reactor equipped with a mechanical stirrer and immersed in a thermostatic bath. 3.24 g of silica (previously calcined at 800° C. and with a concentration of OH groups of 0.78 mmol/g) are slurried with 50 ml of dry toluene. 1.45 g of [(ClSiMe$_2$)(C$_5$H$_4$)](C$_5$H$_5$)ZrCl$_2$ are added to the suspension under inert atmosphere. The reaction mixture is heated to 70° C. and kept under constant stirring during 24 h. At the end the solid is filtered, washed several times with the dry toluene and dried under vacuum. The so obtained violet solid contains 4.38% by weight of Zr. This catalyst component, when stored under nitrogen, is stable for a long time. This catalyst component is named Catalyst A.

Example 4

This example illustrates the preparation of a catalyst component supported onto an inorganic support containing a controlled amount of OH groups. The impregnation reaction of the metallocene onto the inorganic support is carried out according to the procedure of example 3 but using 4.46 g of silica (calcined at 800° C., 0.78 mmol OH/g support) and 0.63 g of [(ClSiMe$_2$)(C$_5$H$_4$)]$_2$ZrCl$_2$. The so obtained grey-greenish solid contains 2.00% by weight of Zr. This catalyst component, when stored under nitrogen, is stable for a long time. This catalyst component is named: Catalyst B.

Example 5

This example illustrates the preparation of a catalyst component supported onto an inorganic support containing a controlled amount of OH groups. The impregnation reaction of the metallocene onto the inorganic support is carried out according to the procedure of example 3 but using 4.71 g of aluminium phosphate gel (calcined at 200° C., 1.21 mmol OH/g support) and 1.63 g of [(ClSiMe$_2$)(C$_5$H$_4$)](C$_5$H$_5$)ZrCl$_2$. The violet solid obtained in this way contains 0.78% by weight of zirconium. This catalyst component is named: Catalyst C.

Example 6

This example illustrates the preparation of a catalyst component supported onto an inorganic support containing a controlled amount of OH groups. The impregnation reaction of the metallocene onto the inorganic support is carried out according to the procedure of example 3 but using 1.88 g of silica (calcined at 400° C., 1.56 mmol OH/g support) and 0.21 g of [(ClSiMe$_2$)(C$_5$H$_4$)]$_2$ZrCl$_2$. The so obtained violet solid contains 0.53% by weight of Zr. This catalyst component is named Catalyst D.

Example 7

This example illustrates the preparation of a catalyst component supported onto an inorganic support chemically modified by incorporation of $NH_2$ groups. The impregnation reaction of the metallocene onto the inorganic support is carried out according to the procedure of example 3 but using 5.16 g of functionalized silica prepared according to example 2A and 333.5 mg of [(ClSiMe$_2$)(C$_5$H$_4$)](C$_5$H$_5$)ZrCl$_2$. The beige solid obtained in this way contains 1.07% by weight of zirconium. This catalyst component is named: Catalyst E.

Example 8

This example illustrates the preparation of a catalyst component supported onto an inorganic support chemically modified by incorporation of $NH_2$ groups. The impregnation reaction of the metallocene onto the inorganic support is carried out according to the procedure of example 3 but using 2.94 g of functionalized silica prepared according to example 2A and 250 mg of [(ClSiMe$_2$)(C$_5$H$_4$)]$_2$ZrCl$_2$. The white-yellowish solid obtained in this way contains 1.49% by weight of zirconium. This catalyst component is named: Catalyst F.

Examples 9–21 describe the preparation of α-olefins homo- or copolymers by the use of heterogenous catalytic systems according to the present invention.

Example 9

This example illustrates the preparation of polyethylene by the use of the catalyst component described in example 3. In a 500 ml glass reactor dried and flushed with nitrogen, with an inlet equipped with a septum and a magnetic stirrer 200 ml of dry heptane are introduced in a nitrogen atmosphere. The reactor is immersed in a thermostatic bath and the nitrogen atmosphere is substituted by ethylene. 10.0 mmol of MAO are introduced in the reactor by using a hypodermic syringe. When the dispersion is saturated with ethylene at 40° C. 10.4 mg (0.05 mmol of Zr) of catalyst A are injected into the reactor. After 15 minutes the reaction is stopped by adding methanol acidified with HCl. 1.22 g of polyethylene are obtained. The catalytic activity is 976 kg PE/mol Zr×h×atm.

Example 10

This example illustrates the preparation of polyethylene by the use of the catalyst component of example 4. The procedure is similar to the one described in example 9 but injecting 45.6 mg (0.01 mmol of Zr) of catalyst B. 2.00 g of polymer are obtained. The catalytic activity is 764 kg PE/mol Zr×h×atm.

Example 11

This examples illustrates the preparation of polyethylene by the use of the catalyst component of example 4. The polymerization was carried out in a 1 l reactor. The reaction temperature was 70° C. and the ethylene pressure was 4 atm. 0.4 bar of H$_2$ were added to the reactor before dosing the catalyst in order to control the molecular weight of the polymer. Afterwards 15.0 mmol of MAO and 0.04 mmol of Zr from catalyst B were injected. After 8 minutes of polymerization 34 g of polymer having Mw=15100 and MWD=3.5 were obtained. The catalytic activity was 1800 kg PE/mol Zr×h×atm.

Example 12

This example illustrates the preparation of polyethylene by the use of the catalyst component of example 5. The procedure is similar to the one described in example 9 but injecting 230 mg (0.02 mmol of Zr) of catalyst C. 1.7 g of polymer are obtained. The catalytic activity is 533 kg PE/mol Zr×h×atm.

Example 13

This example illustrates the preparation of polyethylene by the use of the catalyst component of example 5. The procedure is similar to the one described in example 11, but in this case no hydrogen was used. 230 mg of catalyst C were injected. After 5 minutes of polymerization 11 g of polyethylene having Mw=272.394 and MWD=3.8 were obtained. The catalytic activity is 1500 kg PE/mol Zr×h×atm.

Example 14

This example illustrates the preparation of polyethylene by the use of the catalyst component of example 6. The procedure is similar to the one described in example 9 but injecting 0.005 mmol of Zr of catalyst D. 1.02 g of polymer are obtained after 15 minutes of polymerization. The catalytic activity is 816 kg PE/mol Zr×h×atm.

Example 15

This example illustrates the preparation of polyethylene by the use of the catalyst component of example 7. The procedure is similar to the one described in example 9 but injecting 170 mg (0.02 mmol of Zr) of catalyst E. 1.67 g of polymer are obtained after 15 minutes of polymerization. The catalytic activity is 334 kg PE/mol Zr×h×atm.

Example 16

This example illustrates the preparation of polyethylene by the use of the catalyst component of example 7. The procedure is similar to the one described in example 11, but in this case no hydrogen was used. 10.0 mmol of MAO and 170 mg of catalyst E were injected. After 15 minutes of polymerization 5 g of polyethylene having Mw=305.012 and MWD=3.0 were obtained. The catalytic activity is 230 kg PE/mol Zr×h×atm.

Example 17

This example illustrates the preparation of polyethylene by the use of the catalyst component of example 8. The procedure is similar to the one described in example 16, but in this case 122 mg of catalyst F were injected. After 15 minutes of polymerization 13 g of polyethylene having Mw=168.931 and MWD=3.1 were obtained. The catalytic activity is 800 kg PE/mol Zr×h×atm.

Example 18

This example illustrates the preparation of an ethylene-hexene copolymer by the use of the catalyst component of example 4. The copolymer was prepared according to the procedure described in example 11 but adding 1-hexene. The molar ratio 1-hexene:ethylene in the feeding was 1:1. 10.0 mmol of MAO and then 0.03 mmol of Zr from catalyst B were added. After 15 minutes of polymerization 18 g of polyethylene copolymer having Mw=160.336 and MWD=3.4 were obtained. The catalytic activity is 690 kg PE/mol Zr×h×atm. The obtained copolymer contains 1.78% by moles of hexene randomly distributed.

Example 19

This example illustrates the preparation of an ethylene-hexene copolymer by the use of the catalyst component of example 5. The copolymer was prepared according to the procedure described in example 11 but adding 1-hexene. The molar ratio 1-hexene:ethylene in the feeding was 1:1. 15.0 mmol of MAO and then 0.01 mmol of Zr from catalyst C were added. After 10 minutes of polymerization 18 g of polyethylene copolymer having Mw=110.343 and MWD=3.0 were obtained. The catalytic activity is 2300 kg PE/mol Zr×h×atm. The obtained copolymer contains 1.4% by moles of hexene randomly distributed.

Example 20

This example illustrates the preparation of an ethylene-hexene copolymer by the use of the catalyst component of example 8. The copolymer was prepared according to the procedure described in example 11 but adding 1-hexene. The molar ratio 1-hexene:ethylene in the feeding was 1:1.

10.0 mmol of MAO and then 0.02 mmol of Zr from catalyst F were added. After 15 minutes of polymerization 15 g of polyethylene copolymer having Mw=63.038 and MWD=2.5 were obtained. The catalytic activity is 800 kg PE/mol Zr×h×atm. The obtained copolymer contains 1.2% by moles of hexene randomly distributed.

Example 21

This example illustrates the preparation of an ethylene-octene copolymer by the use of the catalyst component of example 7. The copolymer was prepared according to the procedure described in example 11 but adding 1-octene. The molar ratio 1-octene:ethylene in the feeding was 1:1. 10.0 mmol of MAO and then 0.03 mmol of Zr from catalyst E were added. After 15 minutes of polymerization 6 g of polyethylene copolymer having Mw=106.060 and MWD=3.0 were obtained. The catalytic activity is 250 kg PE/mol Zr×h×atm. The obtained copolymer contains 1.43% by moles of octene randomly distributed.

This invention is related to a method for the preparation of heterogeneous catalysts, useful for the production of polyolefins. The method is characterized because said catalysts are obtained by supporting on solids soluble metallocenes possessing one or more functional groups. Said functional groups are characterized because they can react with other reactive groups on the surface of the solids. The reactive groups on the solids can be part of said solids or incorporated by means of chemical modification. These catalyst systems are especially appropriate for the polymerization of one or several 1-olefins having from 2 to 20 carbon atoms in their chain. Further, they are especially appropriate for the copolymerization of ethylene with 1-olefins having from 3 to 20 carbon atoms in their chains. These polymerization processes can be carried out in gas-phase, slurry or solution, at high temperatures and pressures.

What is claimed is:

1. A catalyst comprising a cocatalyst and a catalyst component obtained by contacting a silicon-containing metallocene compound with an inorganic support to chemically bond the metallocene compound to the inorganic support, wherein the silicon-containing metallocene compound has a formula (I):

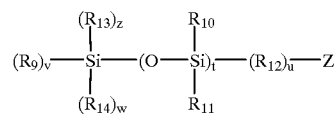

wherein:
M is a metal selected from group 4, 5, or 6 of the periodic table;
each X is independently selected from the group consisting of hydrogen, halogen, $C_1$–$C_{10}$ alkyl, $C_1$–$C_{10}$ alkoxy, $C_6$–$C_{10}$ aryl, $C_6$–$C_{10}$ aryloxy, $C_2$–$C_{10}$ alkenyl, $C_7$–$C_{40}$ arylalkyl, $C_7$–$C_{40}$ alkylaryl, and $C_8$–$C_{40}$ arylalkenyl;
$A_1$ and $A_2$ are independently selected from the group consisting of cyclopentadienyl, substituted cyclopentadienyl, indenyl, fluorenyl, substituted indenyl, and substituted fluorenyl, wherein the substituents are independently $C_1$–$C_{10}$ linear or branched alkyl, $C_5$–$C_7$ cycloalkyl, optionally substituted by an alkyl group, $C_6$–$C_{10}$ aryl, $C_6$–$C_{10}$ aryloxy, $C_2$–$C_{10}$ alkenyl, $C_7$–$C_{40}$ arylalkyl, $C_7$–$C_{40}$ alkylaryl, or $C_8$–$C_{40}$ arylalkenyl;

$R_1$, $R_2$, $R_3$, $R_4$, $R_5$, and $R_7$ are independently hydrogen, $C_1$–$C_{10}$ linear or branched alkyl, $C_5$–$C_7$ cycloalkyl optionally substituted by a $C_1$–$C_6$ alkyl, $C_6$–$C_{10}$ aryl, $C_2$–$C_{10}$ alkenyl, $C_7$–$C_{40}$ arylalkyl, $C_7$–$C_{40}$ alkylaryl, or $C_8$–$C_{40}$ arylalkenyl;
$R_6$ and $R_8$ are independently hydrogen, $C_1$–$C_{10}$ linear or branched alkyl, $C_5$–$C_7$ cycloalkyl optionally substituted by a $C_1$–$C_6$ alkyl, $C_6$–$C_{10}$ aryl, $C_2$–$C_{10}$ alkenyl, $C_7$–$C_{40}$ arylalkyl, $C_7$–$C_{40}$ alkylaryl, $C_8$–$C_{40}$ arylalkenyl, or Q, wherein Q is selected from the group consisting of halogen, amino, alkylamino, and hydroxy;
o, p, q, r, and s are from 0 to 10;
wherein s is not 0 when o is 0; and
m=0 or 1, n=1 or 2, and h=2 or 3, such that m+n+h=4;
and wherein the inorganic support contains hydroxy groups or wherein the inorganic support, prior to being contacted with the metallocene compound, is modified by reaction of hydroxy groups of the support with a compound of formula (II):

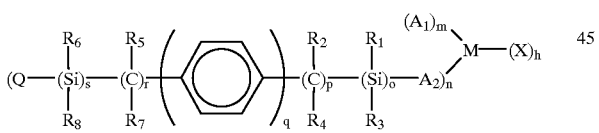

wherein:
$R_9$ is halogen or OR, wherein R is $C_1$–$C_{10}$ linear or branched alkyl, $C_5$–$C_7$ cycloalkyl optionally substituted by a $C_1$–$C_6$ alkyl, $C_6$–$C_{10}$ aryl, $C_2$–$C_{10}$ alkenyl, $C_7$–$C_{.}$arylalkyl, $C_7$–$C_{40}$ alkylaryl, or $C_8$–$C_{40}$ arylalkenyl;
$R_{10}$, $R_{11}$, $R_{13}$, and $R_{14}$ are independently hydrogen, $C_1$–$C_6$ linear or branched alkyl, $C_5$–$C_7$ cycloalkyl, $C_6$–$C_{10}$ aryl, $C_2$–$C_{10}$ alkenyl, $C_7$–$C_{40}$ arylalkyl, $C_7$–$C_{40}$ alkylaryl, $C_8$–$C_{40}$ arylalkenyl, $C_1$–$C_{10}$ alkoxy, or aryloxy;
each $R_{12}$ is independently $C_1$–$C_6$ linear or branched alkylene, $C_5$–$C_7$ cycloalkylene, $C_6$–$C_{10}$ arylene, $C_2$–$C_{10}$ alkylene, $C_7$–$C_{40}$ arylalkylene, $C_7$–$C_{40}$ alkylarylene, or $C_8$–$C_{40}$ arylalkenylene;
Z is selected from the group consisting of $NH_2$, NHR, SH, OH, PHR, Cl, Br, and I, wherein R is defined above;
v+z+w=3 with v different 0; and
t and u are from 0 to 10;
and wherein the inorganic support has a surface area, a pore volume, and an average particle size, the surface area of the inorganic support being 10–1000 $m^2$/g, the pore volume of the inorganic support being 0.2–4.0 $cm^3$/g, the average particle size of the inorganic support being 1–1000 microns.

2. A catalyst according to claim 1, wherein M is Ti, Zr or Hf; $A_1$ and $A_2$ are cyclopentadienyl rings; Q is Cl or Br; and X is Cl.

3. A catalyst according to claim 1, wherein Z is selected from the group consisting of OH, $NH_2$, and SH.

4. A catalyst according to claim 1, wherein the compound of formula (II) is selected from the group consisting of 3-mercaptopropyltrimethoxysilane, 3-aminopropyltrimethoxysilane, N-phenylaminopropyltrimethoxysilane, N-methylaminopropyltrimethoxysilane, 3-chloropropyltrimethoxysilane, and N-aminopropyldimethoxymethylsilane.

5. A catalyst according to claim 1, wherein the cocatalyst is selected from the group consisting of methylalumoxane, boron compounds, and mixtures thereof.

6. A catalyst according to claim 1, wherein the metallocene compound is chemically bonded to the inorganic support by a chemical reaction between the metallocene compound and the Z groups or the hydroxy groups of the inorganic support.

7. A catalyst according to claim 6, wherein the compound of formula (II) is selected from the group consisting of 3-mercaptopropyltrimethoxysilane, 3-aminopropyltrimethoxysilane, N-phenylaminopropyltrimethoxysilane, N-methylaminopropyltrimethoxysilane, 3-chloropropyltrimethoxysilane, and N-aminopropyldimethoxymethylsilane.

8. A catalyst according to claim 1, wherein the surface area of the inorganic support is 150–650 $m^2/g$, the pore volume of the inorganic support is 0.6–2.7 $cm^3/g$, and the average particle size of the inorganic support is 5–100 microns.

9. A catalyst according to claim 8, wherein the metallocene compound is chemically bonded to the inorganic support by a chemical reaction between the metallocene compound and the Z groups or the hydroxy groups of the inorganic support.

10. A catalyst according to claim 2, wherein Z is selected from the group consisting of OH, $NH_2$, and SH.

11. A catalyst according to claim 10, wherein the cocatalyst is selected from the group consisting of methylalumoxane, boron compounds, and mixtures thereof.

12. A catalyst according to claim 2, wherein the metallocene compound is chemically bonded to the inorganic support by a chemical reaction between the metallocene compound and the Z groups or the hydroxy groups of the inorganic support.

13. A catalyst according to claim 12, wherein the cocatalyst is selected from the group consisting of methylalumoxane, boron compounds, and mixtures thereof.

14. A catalyst according to claim 2, wherein the surface area of the inorganic support is 150–650 $m^2/g$, the pore volume of the inorganic support is 0.6–2.7 $cm^3/g$, and the average particle size of the inorganic support is 5–100 microns.

15. A catalyst according to claim 2, wherein the cocatalyst is selected from the group consisting of methylalumoxane, boron compounds, and mixtures thereof.

16. A catalyst according to claim 2, wherein the compound of formula (II) is selected from the group consisting of 3-mercaptopropyltrimethoxysilane, 3-aminopropyltrimethoxysilane, N-phenylaminopropyltrimethoxysilane, N-methylaminopropyltrimethoxysilane, 3-chloropropyltrimethoxysilane, and N-aminopropyldimethoxymethylsilane.

17. A catalyst according to claim 3, wherein the metallocene compound is chemically bonded to the inorganic support by a chemical reaction between the metallocene compound and the Z groups or the hydroxy groups of the inorganic support.

18. A catalyst according to claim 17, wherein the cocatalyst is selected from the group consisting of methylalumoxane, boron compounds, and mixtures thereof.

19. A catalyst according to claim 3, wherein the cocatalyst is selected from the group consisting of methylalumoxane, boron compounds, and mixtures thereof.

20. A catalyst according to claim 3, wherein the surface area of the inorganic support is 150–650 $m^2/g$, the pore volume of the inorganic support is 0.6–2.7 $cm^3/g$, and the average particle size of the inorganic support is 5–100 microns.

21. A catalyst according to claim 5, wherein the metallocene compound is chemically bonded to the inorganic support by a chemical reaction between the metallocene compound and the Z groups or the hydroxy groups of the inorganic support.

22. A catalyst according to claim 5, wherein the surface area of the inorganic support is 150–650 $m^2/g$, the pore volume of the inorganic support is 0.6–2.7 $cm^3/g$, and the average particle size of the inorganic support is 5–100 microns.

23. A catalyst according to claim 5, wherein the compound of formula (II) is selected from the group consisting of 3-mercaptopropyltrimethoxysilane, 3-aminopropyltrimethoxysilane, N-phenylaminopropyltrimethoxysilane, N-methylaminopropyltrimethoxysilane, 3-chloropropyltrimethoxysilane, and N-aminopropyldimethoxymethylsilane.

* * * * *